US007359563B1

(12) United States Patent
Dua et al.

(10) Patent No.: US 7,359,563 B1
(45) Date of Patent: Apr. 15, 2008

(54) METHOD TO STABILIZE A MOVING IMAGE

(75) Inventors: Sumeet Dua, Ruston, LA (US); Roger W. Beuerman, New Orleans, LA (US)

(73) Assignees: Louisiana Tech University Research Foundation, Ruston, LA (US); The Board of Supervisors of LSU, Baton Rouge, LA (US)

( * ) Notice: Subject to any disclaimer, the term of this patent is extended or adjusted under 35 U.S.C. 154(b) by 526 days.

(21) Appl. No.: 10/818,321

(22) Filed: Apr. 5, 2004

(51) Int. Cl.
*G06K 9/40* (2006.01)
(52) U.S. Cl. ....................................... 382/254
(58) Field of Classification Search ................. 382/254
See application file for complete search history.

(56) References Cited

U.S. PATENT DOCUMENTS

| | | | | |
|---|---|---|---|---|
| 4,856,891 A | * | 8/1989 | Pflibsen et al. | 351/210 |
| 5,644,642 A | * | 7/1997 | Kirschbaum | 382/103 |
| 5,767,941 A | * | 6/1998 | Ferguson | 351/206 |
| 6,188,728 B1 | * | 2/2001 | Hurst | 375/240.16 |
| 6,283,954 B1 | * | 9/2001 | Yee | 606/5 |
| 6,452,969 B1 | * | 9/2002 | Yim | 375/240.02 |
| 6,736,508 B2 | * | 5/2004 | Xie et al. | 351/209 |
| 6,758,564 B2 | * | 7/2004 | Ferguson | 351/221 |
| 6,937,659 B1 | * | 8/2005 | Nguyen et al. | 375/240.19 |
| 7,113,818 B2 | * | 9/2006 | Podoleanu et al. | 600/476 |
| 2005/0024586 A1 | * | 2/2005 | Teiwes et al. | 351/209 |
| 2005/0140984 A1 | * | 6/2005 | Hitzenberger | 356/497 |

OTHER PUBLICATIONS

Denis Laurin et al., "Three-dimensional object tracking using a Fourier transform of sine-coded range images," Optical Engineering, Jun. 1995, vol. 34 No. 6.*

Daniel Hammer et al., "Active retinal tracker for clinical optical coherence tomography systems," Journal of Biomedical Optics vol. 10(2), Mar./Apr. 2005.*

Daniel Hammer et al., "Image stabilization for scanning laser ophtalmoscopy," Optics Express vol. 10 No. 26, Dec. 2002.*

(Continued)

*Primary Examiner*—Jingge Wu
*Assistant Examiner*—Jeffrey S Smith
(74) *Attorney, Agent, or Firm*—Jones, Walker, Waechter Poitevent, Carrere & Denegre, L.L.P.

(57) ABSTRACT

The invention is a process to compare two digital images (and usually more) and to identify objects in each image. After object identification, object descriptors are formed. The object descriptors of the objects in one frame are compared to those of objects in the second frame, allowing the tracking of an object in the two frames. The movement of each tracked object within the two frames is quantified, and the second frame is corrected to account for the object's movement.

25 Claims, 21 Drawing Sheets

OTHER PUBLICATIONS

Espen Naess et al., "Computer-assisted laser photocoagulation of the retina-a hybrid tracking approach," Journal of Biomedical Optics, vol. 7 No. 2, Apr. 2002.*

Agrawal, R., Faloutsos, C., and Swani, A.N., 1993 Efficient Similarity Search in Sequence Databases. In Proceedings of the 4th International Conference on Foundations of Data Organization and Algorithms (Oct. 13-15, 1993), D.B. Lome, Ed Lecture Notes in Computer Science vol. 730 Springer-Verlag, London, 69-84.

Plebe, A. and Gallo, G., "Filtering echocardiographic image sequences in frequency domain," Image and Signal Processing and Analysis, 2001. ISPA 2001 Proceedings of the 2nd Int'l Symposium on, vol., No., pp. 238-243, 2001.

Beauchemin, S. S. and Barron, J. L. 2000. On the Fourier Properties of Discontinuous Motion. J. Math. Imaging Vis. 13, (Dec. 3, 2000), 155-172.

Sellis, T.K., Roussopoulos, N., and Faloutsos, C. 1987. The R+- Tree A Dynamic Index for Multi-Dimensional Objects. In Proceedings of the 13th Int'l Conf. on Very Large Data Bases (Sep. 1-4, 1987). P.M. Stocker, W. Kent, and P. Hammersley, Eds. Very Large Data Bases. Morgan Kaufmann Publishers, San Francisco, CA, 507-518.

Wagstaff, K., Cardie, C., Rogers, S., and Schrodl, S. 2001. Constrained K-means Clusterin with Background Knowledge. In Proceedings of the Eighteenth International Conference on Machine Learning (Jun. 28,-Jul. 10, 2001). C.E. Brodley and A. P. Danyluk, Eds. Morgan Kaufmann Publishers, San Francisco, CA, 577-584.

He, Chao; Zheng, Yuan F.; Ahalt, Stanely C.: Object tracking using the Gabor wavelet transform and the golden section algorithm. IEEE Transactions on Multmedia 4(4); 528-538 (2002).

Guidry, Diana L., Farag, Aly A.: Using Active Contours and Fourier Descriptors for Motion Tracking with Applications in MRI. ICIP (2) 1999: 177-181.

Bobick, A.F. and Bolles, R.C. 1992. The Representation Space Paradigm of Concurrent Evolving Object Descriptions. IEEE Trans. Pattern Anal. Mach. Intell. 14, (Feb. 2, 1992), 146-156.

* cited by examiner

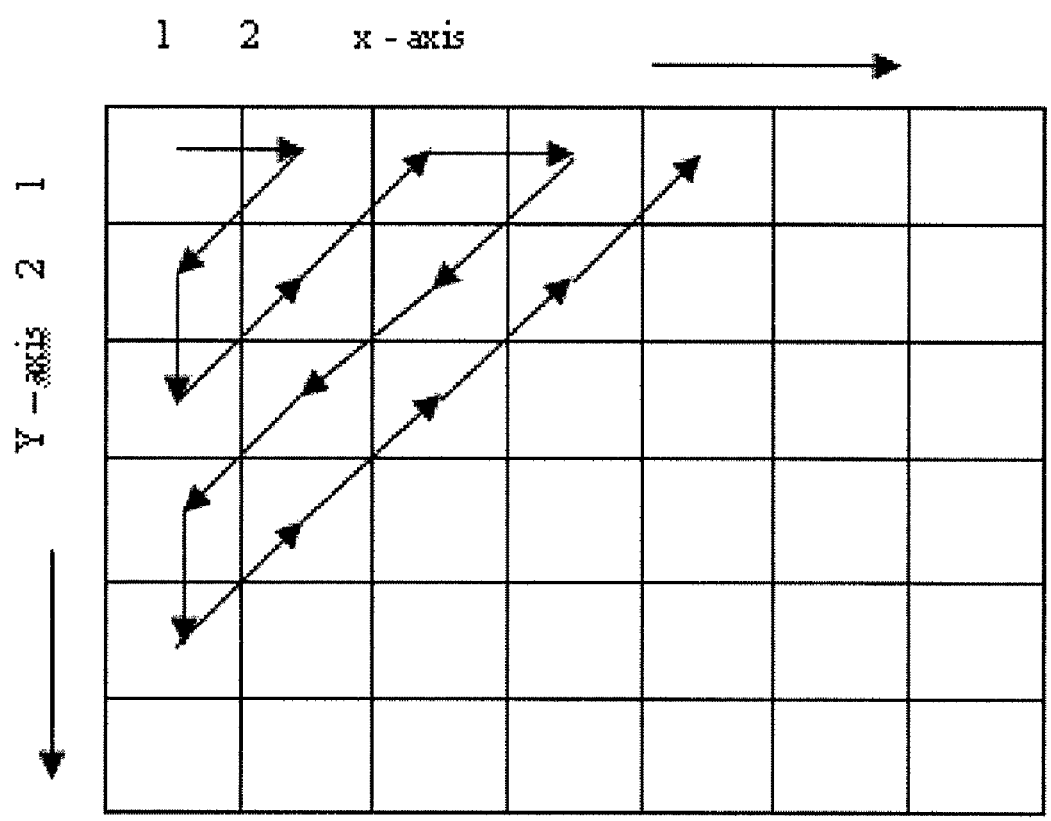
Figure 4: Zig-zag sampling procedure from an image

Figure 5: Portion of the time-domain representation of the zig-zag sampled signal from frame in

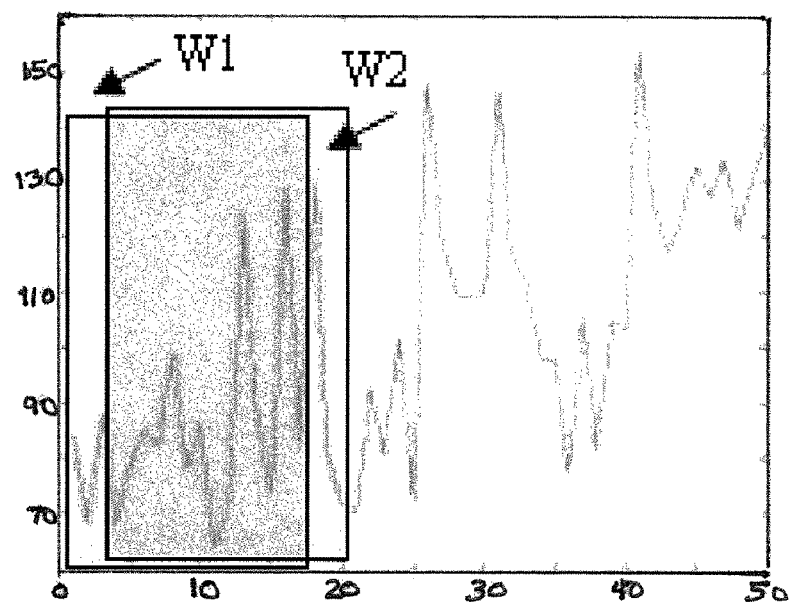
Figure 6: Window extraction procedure from the one-dimensional Zig-zag signal

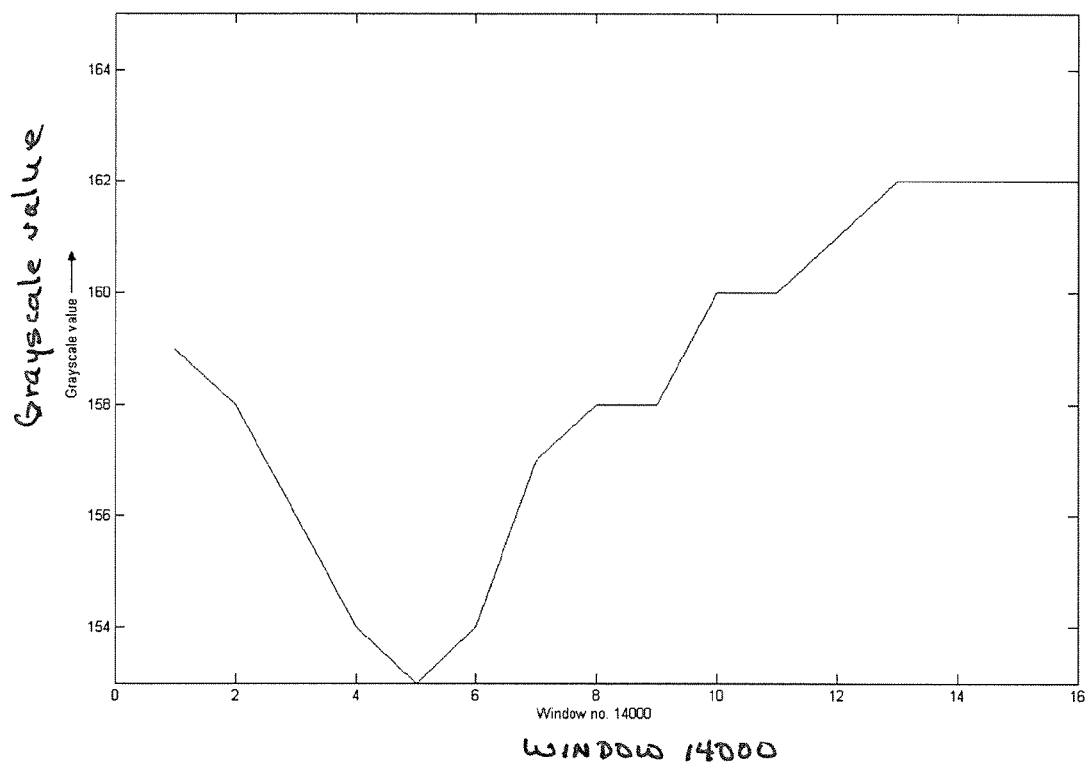
Figure 7: A sample window of size 16 (window number 14000) in time domain

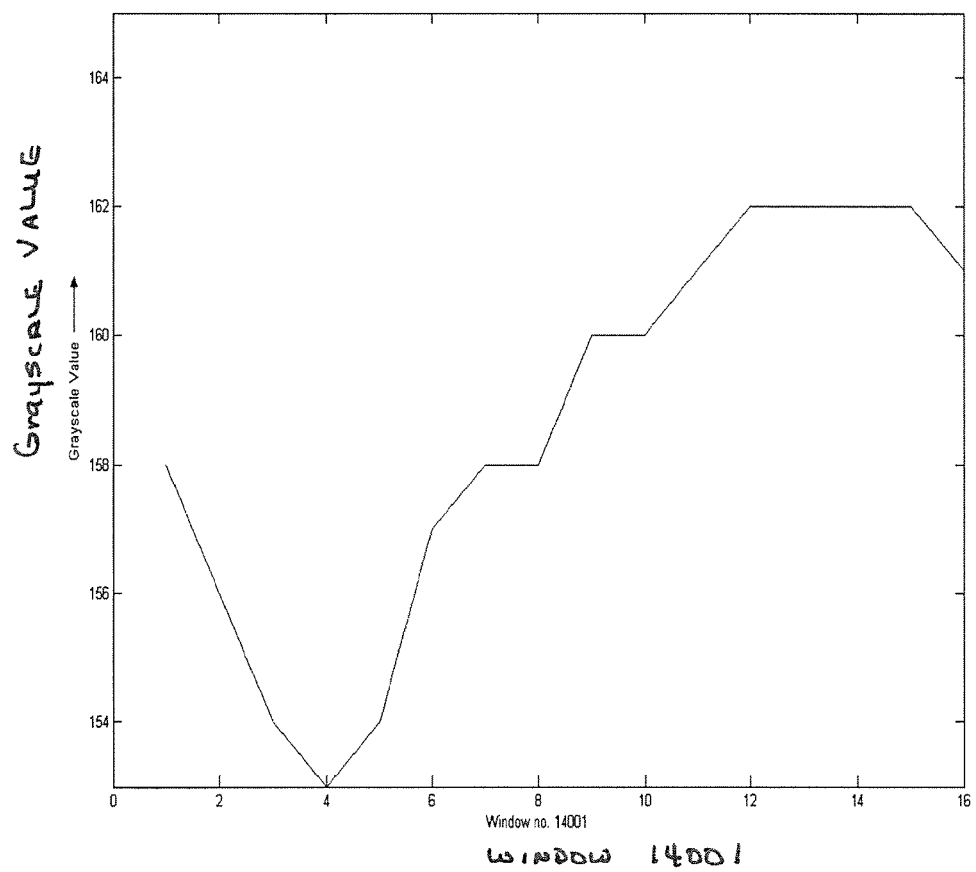
Figure 8: A consecutive sample window of size 16 (window number 14001) in time domain

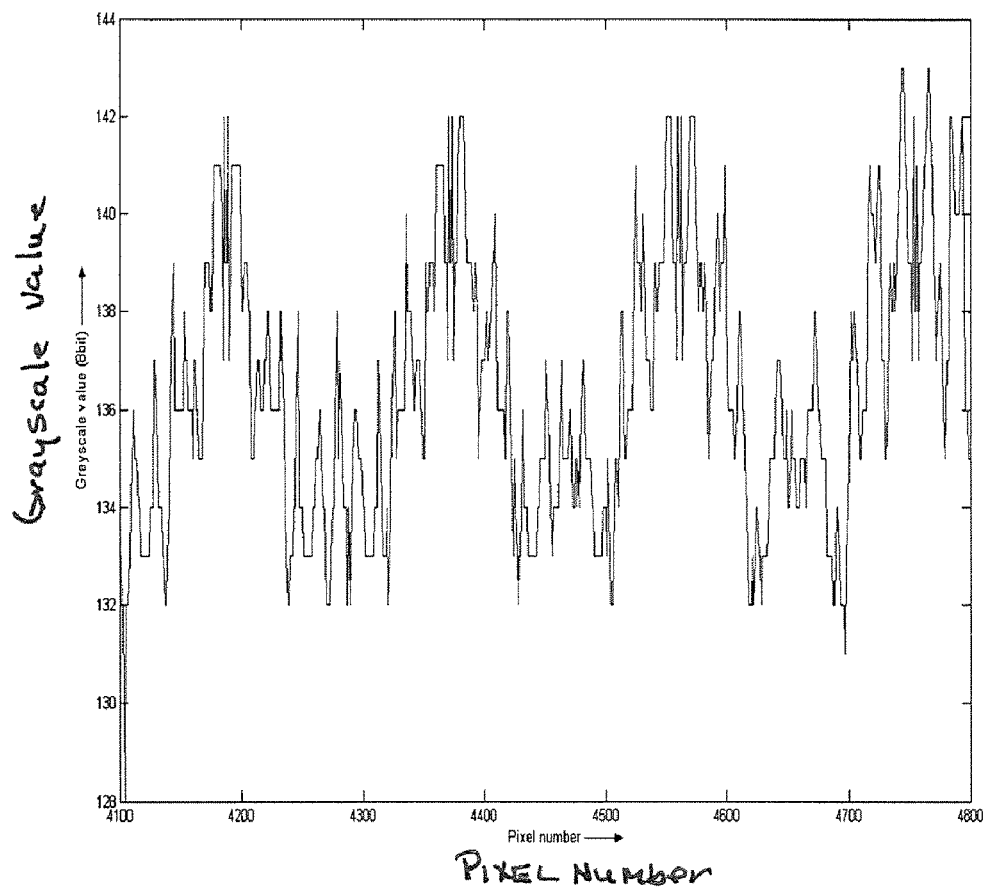
Figure 9: Time-domain representation of the portion of the zig-zag sampled signal

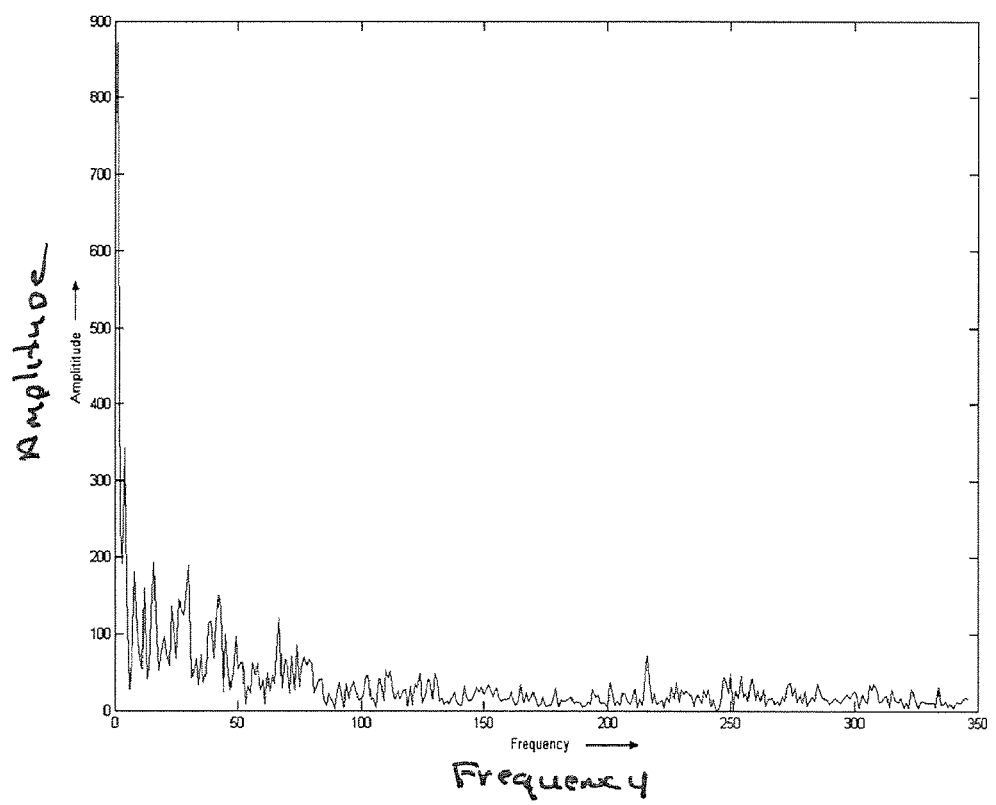
Figure 10: Amplitude of the real part of the Fourier frequency spectrum of the signal presented in Figure 9. Note the skewed energy spectrum in the plot

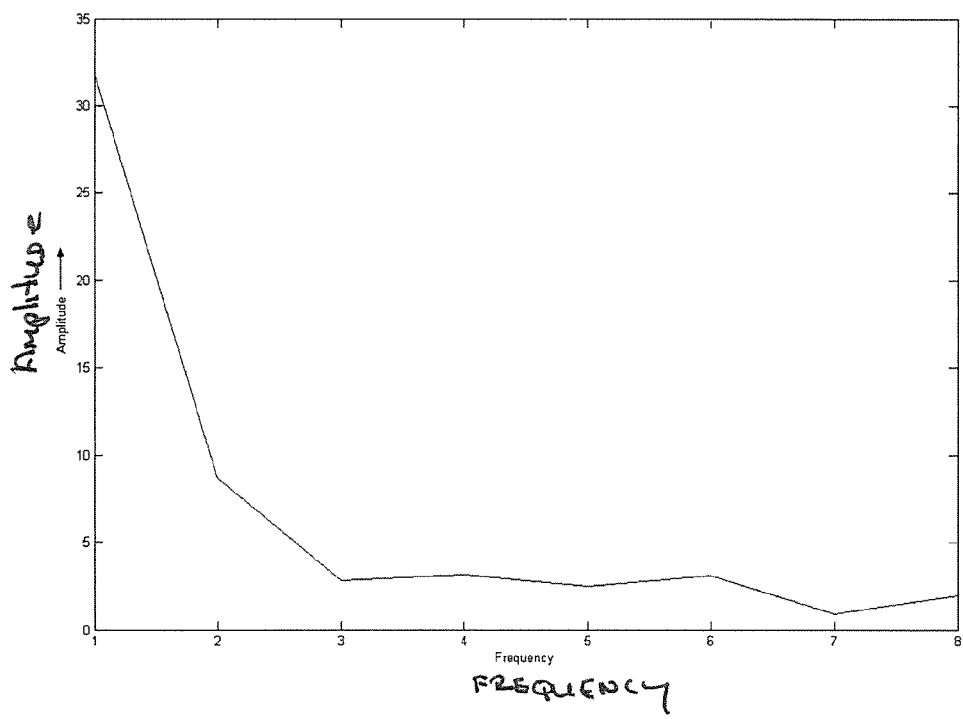
Figure 11: Amplitude of the real part of the Fourier frequency spectrum (8 points, ignoring the redundant symmetric part) of the window presented in Figure 7.

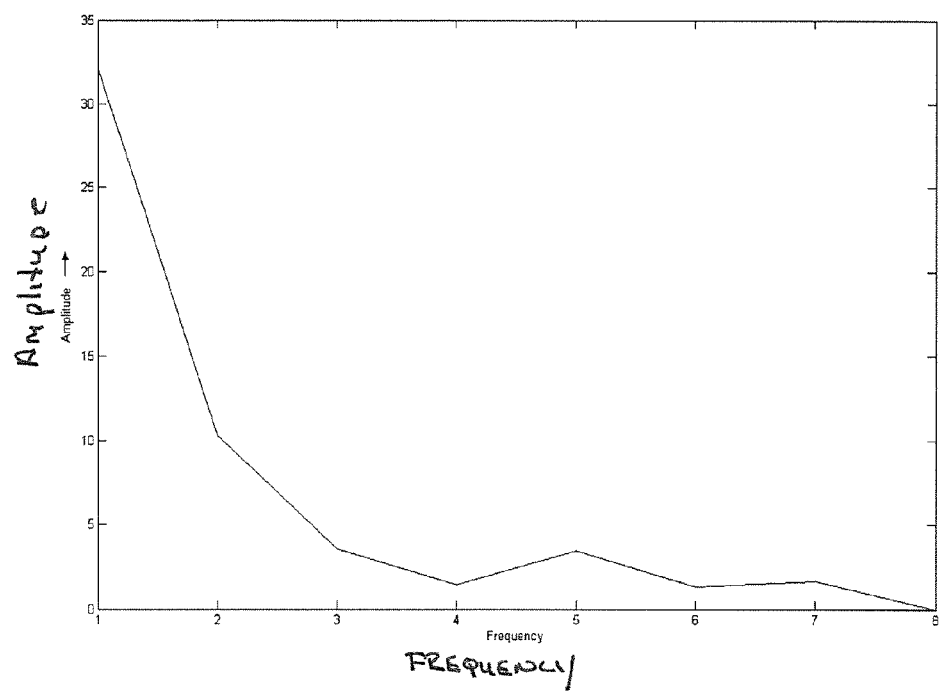
Figure 12: Amplitude of the real part of the Fourier frequency spectrum (8 points, ignoring the redundant symmetric part) of the window presented in Figure 8.

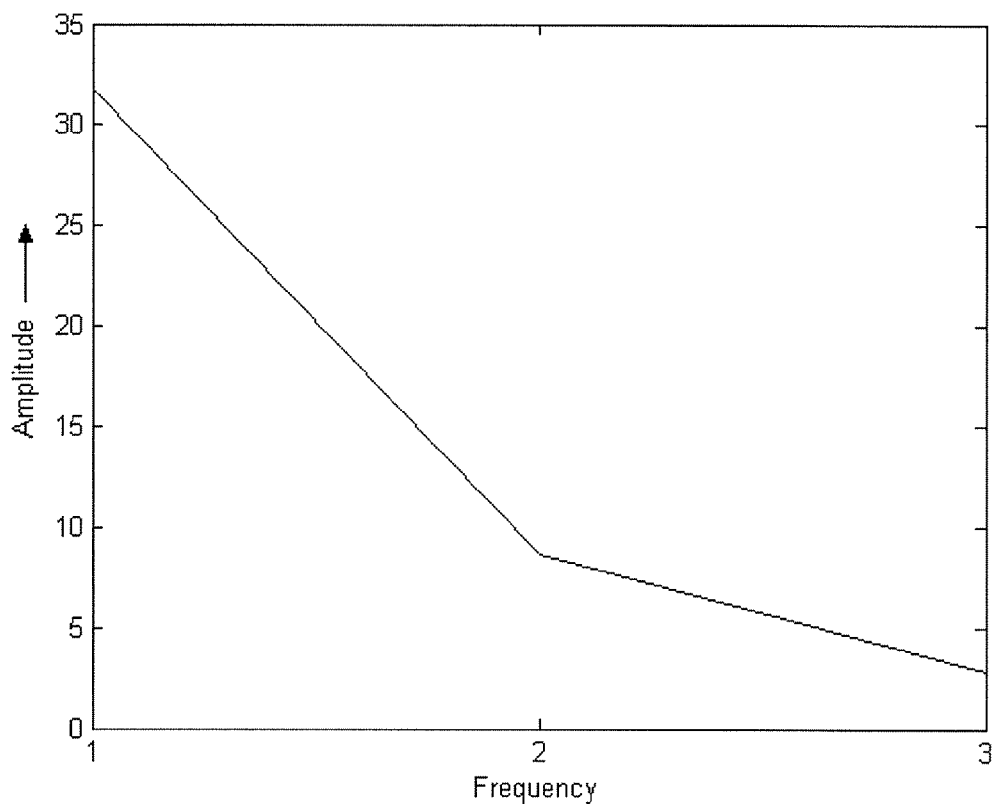
Figure 13: Amplitude of the real part of the Fourier frequency spectrum (8 points, ignoring the redundant symmetric part) of the window presented in Figure 7 after preserving first few frequencies.

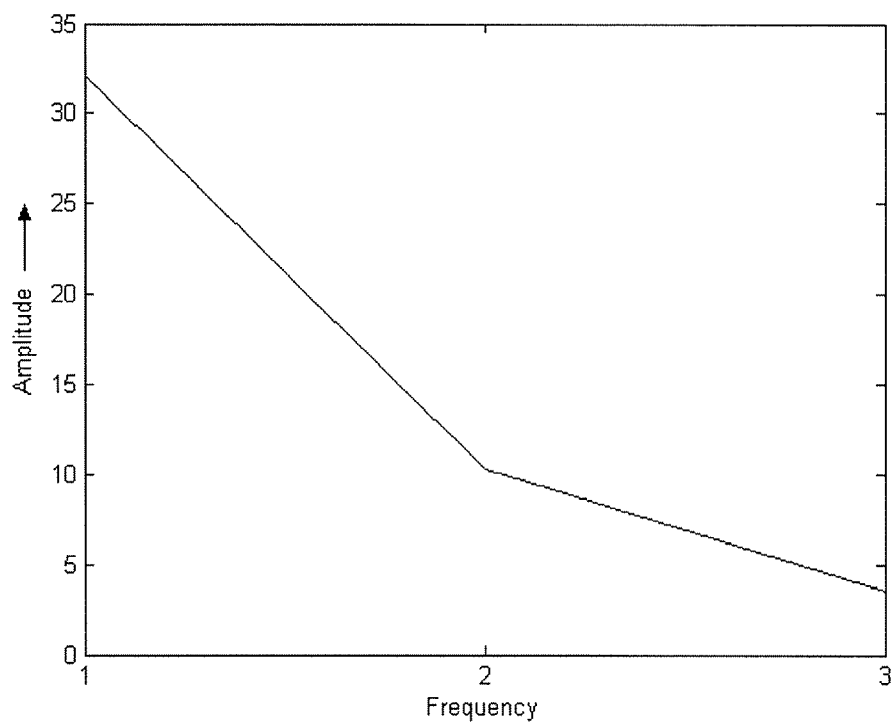
Figure 14: Amplitude of the real part of the Fourier frequency spectrum (8 points, ignoring the redundant symmetric part) of the window presented in Figure 8 after preserving first few frequencies.

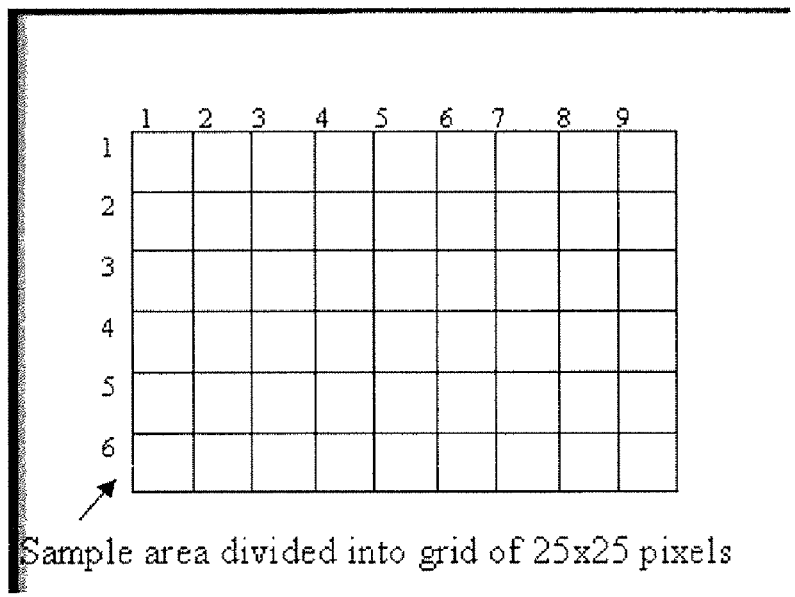
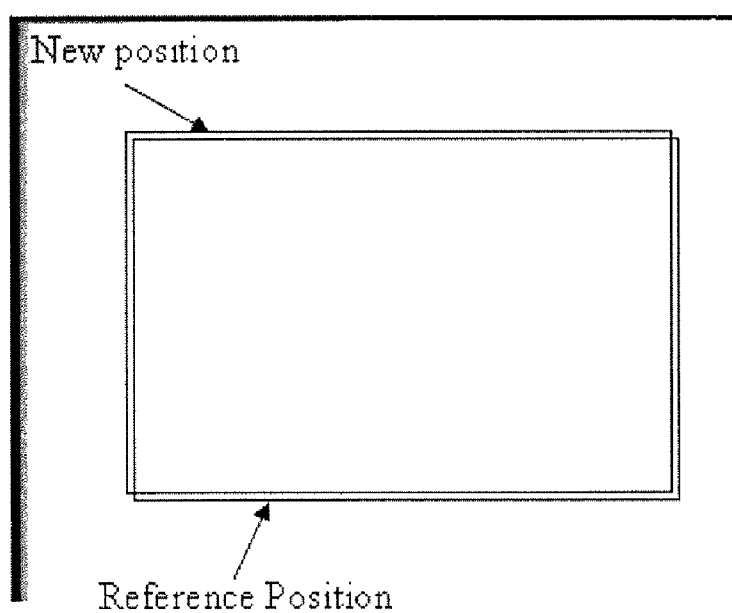
Figure 15 Error vector computation using local-zoning procedure.

| Column → | | | | | | | | | |
|---|---|---|---|---|---|---|---|---|---|
| Row | 1 | 2 | 3 | 4 | 5 | 6 | 7 | 8 | 9 |
| 1 | 68.42 | 86.48 | 86.66 | 66.66 | 70.00 | 88.67 | 50.00 | 14.28 | NA |
| 2 | 86.36 | 79.59 | 90.00 | 66.66 | 75.00 | 69.23 | 38.46 | 88.57 | 0 |
| 3 | 11.11 | 80.95 | 90.00 | 78.82 | 78.57 | 65.71 | 85.41 | 73.07 | 100.00 |
| 4 | 77.41 | 100.00 | 75.47 | 71.76 | 84.37 | 60.00 | 80.00 | 41.66 | 50.00 |
| 5 | 00.00 | 60.00 | 75.00 | 85.18 | 00.00 | 60.00 | 56.52 | 45.45 | NA |
| 6 | 55.55 | 62.50 | 57.14 | NA | 16.66 | 30.00 | 52.00 | 33.33 | NA |

*NA – implies absence of MER in that window of grid*

Figure 16: Corresponding percentage of MER match for each of the zones described in Figure 15.

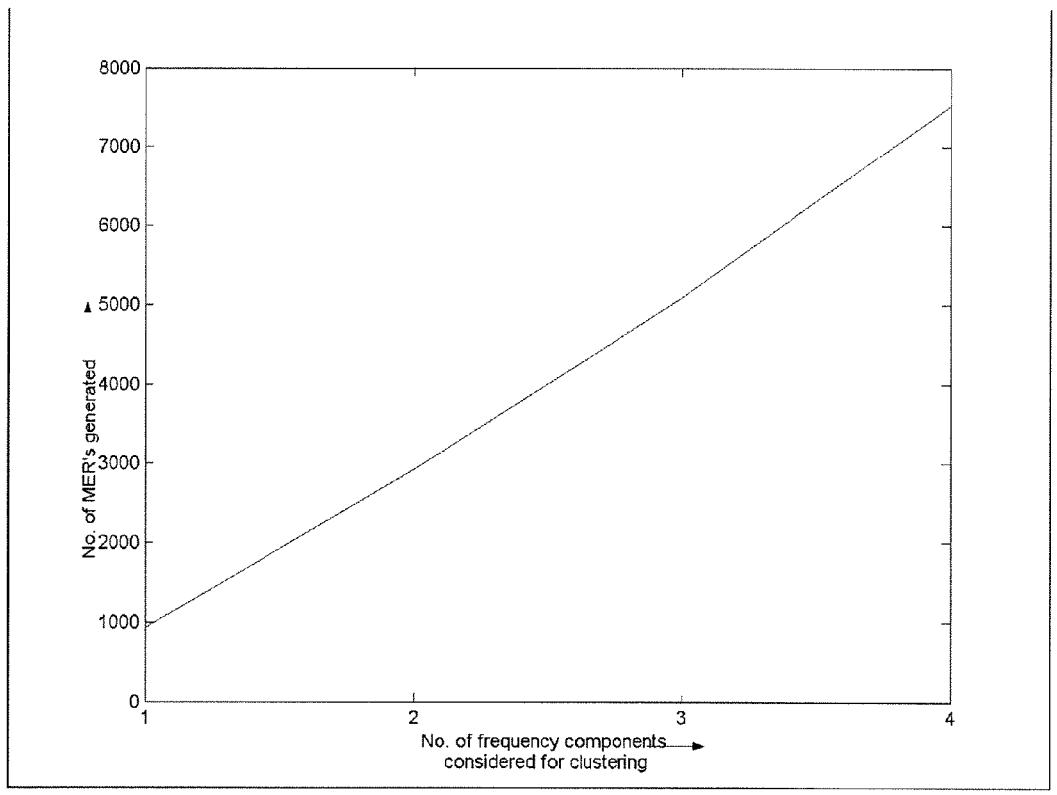
Figure 17: Effect of increasing number of Fourier frequency coefficients on the total number of MERs generated for similarity match

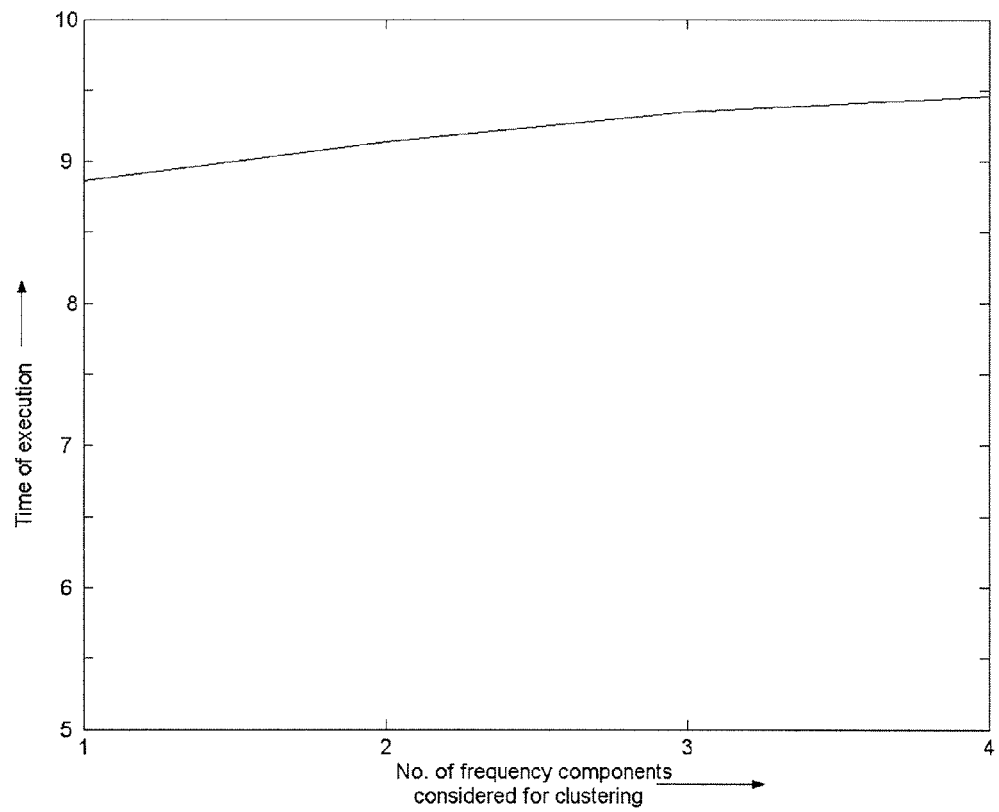
Figure 18: Effect of increasing number of Fourier frequency coefficients on the total time of execution of the similarity matching procedure

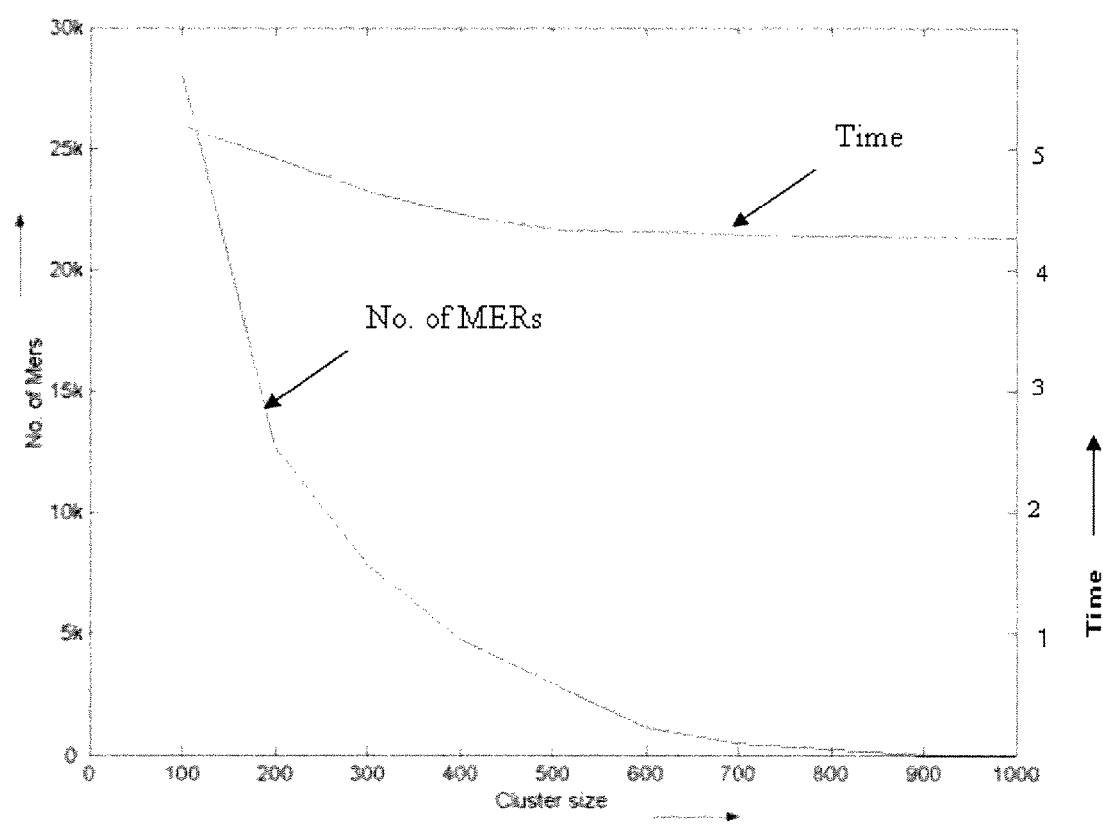
Figure 19: Effect of Cluster size on the number of MERs and execution time

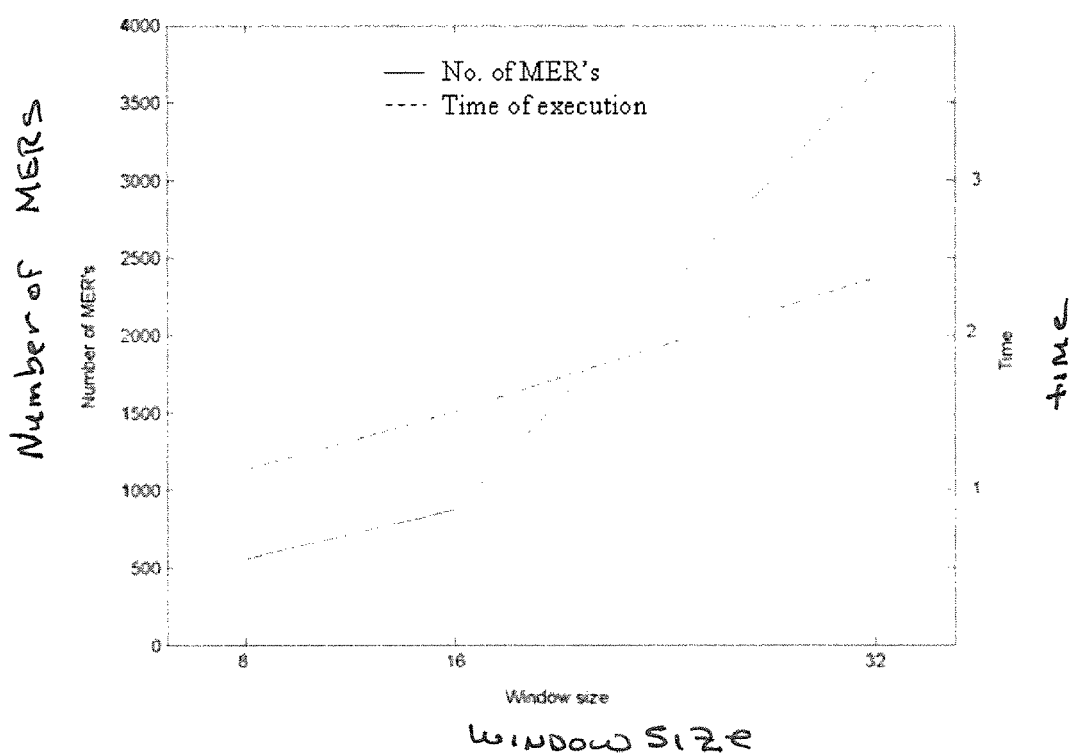
Figure 20: Effect of Window size on the number of MERs and execution time Figure 21 - Formation of MER Windows for 1-D signal
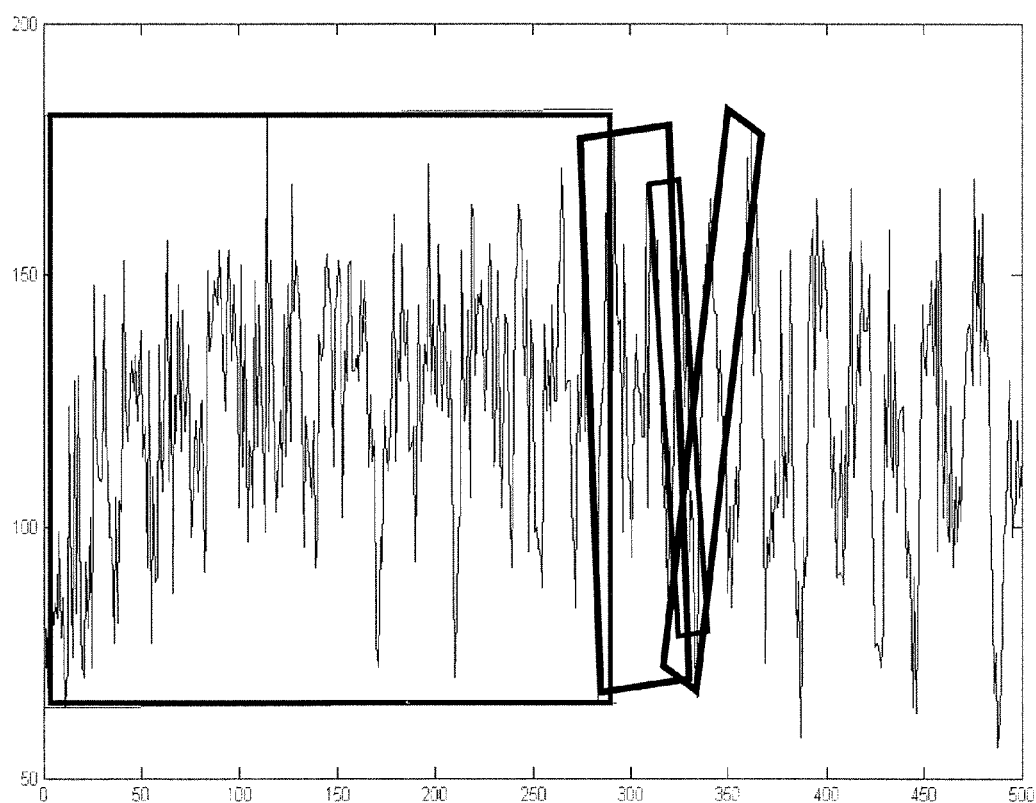

METHOD TO STABILIZE A MOVING IMAGE

COMPUTER PROGRAM LISTING APPENDIX

Attached hereto and incorporated by reference is the computer program listing appendices. The appendices, in accordance with 37 CFR 1.96, are contained on a single compact disk, submitted in duplicate. Each disk submitted has two folders: (1) Window based image stabilization; and (2) Zig-Zag based image stabilization.

A directory of each folder follows:

| Zig-Zag based image stabilization: | | |
|---|---|---|
| Created | | size and name of files |
| Feb. 19, 2003 | 07:51 AM | 2,426 class_mers.m |
| Feb. 19, 2003 | 07:51 AM | 5,041 c_cluster.m |
| Feb. 19, 2003 | 07:51 AM | 334 c_fft.m |
| Feb. 28, 2003 | 03:49 PM | 1,741 c_main.m |
| Feb. 19, 2003 | 07:51 AM | 7,508 c_mer.m |
| Jun. 07, 2003 | 10:34 AM | 18,029 image_comparison.m |
| Mar. 03, 2003 | 03:10 PM | 1,359 kmeans.m |
| Mar. 22, 2003 | 04:54 PM | 2,916 main_script.m |
| Feb. 27, 2003 | 04:38 PM | 264 mark_p.m |
| Feb. 19, 2003 | 07:51 AM | 1,851 p_file3.m |

| Window based image stabilization: | | |
|---|---|---|
| Created | | size and name of files |
| Jun. 07, 2003 | 10:34 AM | 18,029 Image_comparison.m |
| Mar. 03, 2003 | 03:10 PM | 1,359 kmeans.m |
| Jul. 01, 2003 | 04:49 PM | 24,754 main_script.m |

The program is written in MATALB from Mathworks, Inc. and can be executed on an IBM-PC formatted machine operating with Windows XP and Matlab version 6.5.

FIELD OF INVENTION

The invention relates to methods of stabilizing an image, and more particularly to images viewed and recorded through stable microscopes (such as a confocal microscope) when the observed subject may be moving in a non-linear fashion.

BACKGROUND OF THE INVENTION

White light, real-time, scanning confocal microscopes have been used in clinical and investigative opthalmology for many years, and the applications of this technology to patients have expanded and include refractive surgery and use to assist in diagnosis of diseases. In clinical use, a camera can be attached to the confocal microscope, to record the images, and attached to a display device to display the images on a screen in real-time. The microscope and attached camera are generally stable and do not move. However, the eye being observed through the confocal microscope by the ophthalmologist is not necessarily stable or stationary. The subject's eye may move due to the inability of the subject to maintain a totally steady gaze, or due to movements of the subject causing the subject's eyes to move in the observed field. Additionally, portions of the eye being observed can move due to intrinsic biological factors, such as involuntary movements. Such movements may be non-linear in the sense that a movement in one area of the observed field may not be reflected in another area of the observed field. The movement may be localized to a portion of the observed field and other movements reflected in another area of the observed field. These types of movements make the interpretation of the observed images difficult.

In the confocal microscope system, the camera and microscope are stabilized with minimal movements, but the observed eye is constantly moving. Even "minor" movements can become a significant problem as the microscope will magnify the image of the movement. At magnification levels of around 500× that is needed to visualize cellular level details within the eye, it is apparent that a minor eye movement can prevent significant visualization difficulties to the ophthalmologist trying to observe the non-linear moving image field.

Image stabilization has been addressed in the prior art from the standpoint of stabilization of camera movement (such as in hand held video recorders) to prevent a blurring or movement in the imaged field. Additionally, stabilization of cameras on moving platforms observing a relatively still object has been addressed. However, stabilization of the imaged field to account for undesired movement of the imaged subject, particularly a non-linear type of movement, has not been examined and stabilization in this sense presents added difficulties. Non-linear movement is used in the sense that movement in one portion of the observed field may not reflect movement in another portion of the observed field. Prior art stabilization techniques generally apply a global shift or translation of the image, that is, each portion of the image receives the same "correction." With non-linear movement of the subject in the observed or imaged field, global corrections are insufficient to effect image stabilization. A technique is needed to identify and quantify changing areas of an image, and to correct those areas of the image to account for the changes.

SUMMARY

The invention is a process to compare two digital images and to identify objects in each image. After object identification, object descriptors are formed. The object descriptors of the objects in one frame are compared to those of objects in the second frame, allowing the tracking of an object in the two frames. The movement of each tracked object within the two frames is quantified, and the second frame is corrected to account for the object's movement.

OBJECTS OF THE INVENTION

An object of the invention is to enable real-time processing of a series of digital images of a subject to account for movement of the subject in the recorded images.

It is an object of the invention to correct for non-linear movements of the observe subject in a series of digital images of the subject.

It is an object of the invention to identify and track moving objects in a series of digital images.

It is an object of the invention to quantify the movements of a number of objects in a series of digital images, and to correct for the movement.

BRIEF DESCRIPTION OF THE DRAWINGS

FIG. 4: Zig-zag sampling procedure from an image.

FIG. 5: Portion of the time-domain representation of the zig-zag sampled signal from frame in FIG. 1.

FIG. 6: Window extraction procedure from the one-dimensional zig-zag signal.

FIG. 7: A sample window of size 16 (window number 14000) in time-domain.

FIG. 8: A consecutive sample window of size 16 (window number 14001) in time-domain.

FIG. 9: Time-domain representation of the portion of the zig-zag sampled signal.

FIG. 10: Graph displaying the amplitude of the real part of the Fourier frequency spectrum of the signal presented in FIG. 9. Note the skewed energy spectrum in the plot.

FIG. 11: Graph displaying the amplitude of the real part of the Fourier frequency spectrum (8 points, ignoring the redundant symmetric part) of the window presented in FIG. 7.

FIG. 12: Graph displaying the amplitude of the real part of the Fourier frequency spectrum (8 points, ignoring the redundant symmetric part) of the window presented in FIG. 8.

FIG. 13: Graph displaying the amplitude of the real part of the Fourier frequency spectrum (8 points, ignoring the redundant symmetric part) of the window presented in FIG. 7 after preserving first few frequencies.

FIG. 14: Graph displaying the amplitude of the real part of the Fourier frequency spectrum (8 points, ignoring the redundant symmetric part) of the window presented in FIG. 8 after preserving first few frequencies.

FIG. 15: Error vector computation using local-zoning procedure.

FIG. 16: Table showing the corresponding percentage of MER match for each of the zones described in FIG. 15.

FIG. 17: Graph displaying the effect of increasing number of Fourier frequency coefficients on the total number of MERs generated for similarity match.

FIG. 18: Graph displaying the effect of increasing number of Fourier frequency coefficients on the total time of execution of the similarity matching procedure.

FIG. 19: Graph displaying the effect of Cluster size on the number of MERs and execution time.

FIG. 20: Graph displaying the effect of Window size on the number of MERs and execution time.

FIG. 21: Graph showing MER formation with the 1-D signal.

DETAILED DESCRIPTION OF THE INVENTION

Figure 1:
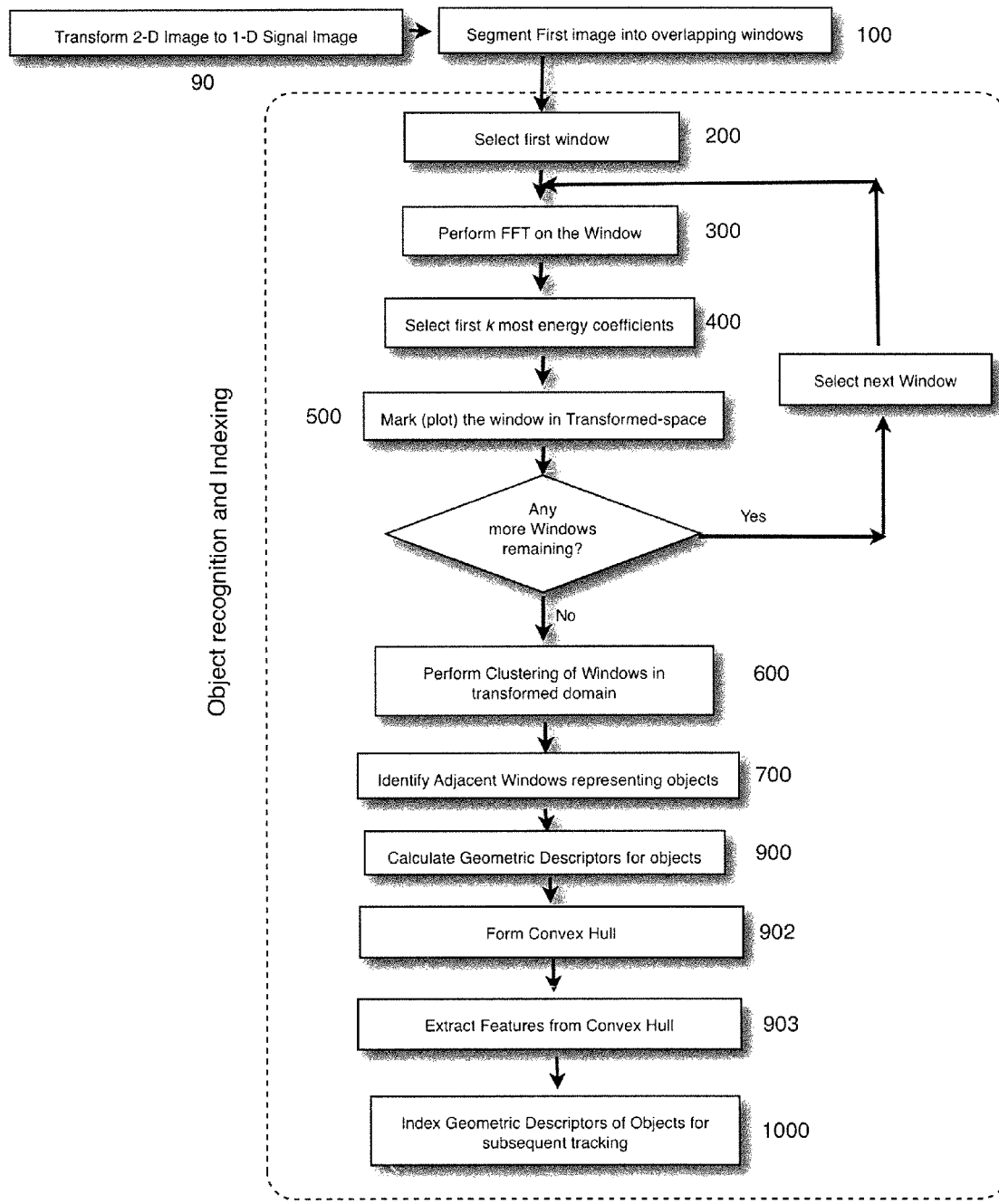
FIG. 1: Is a flow chart showing the method through formation of object descriptors

The invention relates to processing digital images, either an analog image that has been digitized or one captured with a digital camera. As described, the images reflect a digital video image taken through a confocal microscope (29 frames/sec). However, the technique is not limited to use with confocal microscope images. Other types of digital images where the observed field is moving non-linearly can benefit from this technique. Other suitable types of images include various medical images, images captured through telescopes, and other microscope images. The invention as described includes the step of correction or stabilization of adjacent images to account for movement of identified and matched objects in adjacent frames. However, if object identification and tracking in a series of images is all that is required, correction for object movement may not be needed or desired.

The invention can be operated in "real-time" or in a post processing mode on a completed set of images. Real-time processing has constraints placed upon the technique due to limitations in the ability to process or crunch the images in accordance with the technique and maintain an output corrected display that appears to be a real-time video sequence of images. For this reason, a series of depopulation steps are included. As processing capabilities increase, these depopulation steps become less needed. In a post processing mode, the real-time constraints are not as critical, and the depopulation maybe eliminated. The following description will be based upon a "real-time" processing, where "real-time" is understood as follows.

Each individual "image" is a digital representation of the field of view in the focal area of the microscope at a particular point in time. Each image is a two dimensional matrix of pixels, with each pixel having an associate intensity level or gray level. The images are "black and white" images. The images are displayed in a monitor (and may be recorded) for viewing by the attending physician. The images are viewed as a time sequence series of sequential images. "Real-time" processing of the images entails depopulation of the time series of images and processing and modification of the depopulated series prior to display. Hence, there is a delay between the time an image is captured by the microscope and the time the processed image is displayed on the monitor. For real-time processing, the delay can be minimized with suitable depopulation techniques employed on the raw images and in the processing techniques, and the use of high speed processors to execute the stabilization technique.

Finally, the technique as described is employed on "black and white" grayscale images (where the recorded field is a single variable, such as light intensity). However, the technique can be employed on images where a variety of object aspects (such as color components, hue components, etc.) are sampled and recorded. In this event, appropriate modifications should be undertaken in the object recognition portion of the technique, if it is desired to use additional recorded aspect fields to help assist in object identification. One suggested modification would be to utilize a multidimensional data transform in technique 2 to account for the additional recorded aspects, or to create a series of 1-D signals in technique 1, each corresponding to a recorded image aspect. The additional recorded aspects can also be use to utilized images in correction or stabilization.

The techniques will be described in two general configurations, a 1-D signal configuration and a 2-D signal configuration, using the following analytical framework:

A.1 Image Capturing
A.2 Signal Synthesis
A.3 Signal Partition
A.4 Object Recognition
A.5 Formation of Object Descriptors
A.6 Identify Corresponding Objects, Object Tracking
A.7 Formation of Error Vector
A.8 Stabilize Frame Correction)

Each of the above steps is explained as follows.

I FIRST EMBODIMENT

A 1-D Signal Representation

A.1 Image Capturing

The raw unstabilized confocal videos are obtained at the rate of 29 frames/sec. Although theoretically one can extract and process 29 frames from a one-second long video, it is not desirable for the following reasons:
(1) The drifting or destabilization of objects in these frames may not be prominent in subsequent frames, and performing a computational stabilization procedure on subsequent frames is not an efficient use of resources.
(2) Experiments have shown that the stabilization technique employed on adjacent subsequent frames is more susceptible to Gaussian or white noise.

For these reasons, it is more efficient to depopulate the sampled frames. The sample rate should be fine enough to keep the presentation displayed on the monitor from jittering due to too coarse depopulation. The actual depopulation can vary with the application, and one acceptable rate was to depopulate the frame date set by a factor of 6 (use every $7^{th}$ frame in the video) to result in a display rate of approximately 4 frames/sec.

The following should be noted from the given frames:
(1) The objects in these frames are not clearly marked, demarcated or explicit.
(2) The objects move within the frame in subsequently sampled frames.
(3) Each of these objects may move in different directions in subsequently sampled frames.
(4) Each of these objects may scale (due to differential optical illumination) and rotate (to intrinsic movement of these objecs independent of the resident frame) in subsequent sampled frames.
(5) Some objects might be missing in subsequent sampled frames.
(6) Some objects might be new in subsequent sampled frames.

A.2 Signal Synthesis

A digital imaged frame is a two-dimensional signal in the form of a matrix. This two-dimensional matrix represents pixels attributed by row and column numbers with an intensity (0 . . . 255) value associated with the pixel. From this two-dimensional signal, a one-dimensional signal is extracted. In one embodiment, a zig-zag transform is taken of the two-dimensional image. In the zig-zag transform, the values of the two-dimensional signals (the signal intensity associated with the matrix position) are re-posted into a sequential series (step 90, FIG. 1), where the mapping from two-dimensions to one-dimensions is taken along a zig-zag path through the 2-D dataset, one particular transform is shown in FIG. 4. Other 2-D to 1-D mappings could be used, such as reposting along rows or columns. From an image of size m×n, the resulting linear 1-D sequence or signal has a length of mn. FIG. 5 presents a portion (Pixel number 4100 to 4800) of the zig-zag sampled one-dimensional signal from the image.

A.3 Signal Partition

The next step is to partition the resulting 1-D signal. This step groups the signal sequence into overlapping windows of fixed size (step 100, FIG. 1). FIG. 6 depicts the windowing process showing the first two windows (W1 and W2) formed, where the window size is 16 units long, and the overlap is 15 units. The window size or length and the degree of overlap are parameters that are adjustable based upon the data.

Guidelines for choice of window size include the following heuristics:
(1) Too small a window size may bring in discontinuities in object boundaries.
(2) Too small a window size may increase the dimensionality of data, hence making the computational procedure slow and inefficient.
(3) Too small a window size might reduce the correctness of the assumption that the signals within the window display skewed energy spectrum.
(4) Too large a window size may lead to ignoring certain objects that are small, yet important.
(5) Too large a window size may lead to object boundaries that are overlapping, hence making the object recognition procedure non-deterministic.

As can be seen, window size is dependent upon object size. Factors that will influence the window size include:
(1) Source of data: A smaller window is suggested for a relatively stable image in contrast to large window size for destabilized images.
(2) Format of data: a larger window size in a grayscale image may perform equally well as a small window size in a colored image.
(3) Rate of frame sampling: window size is inversely proposal to the rate of sampling of frames.

For the confocal grayscale images examined, a window length of w=8 has yielded suitable results with an overlap of 7 (w−1). For the following results, a window size of 16 was utilized with an overlap of 15. For convenience, the 1-D formed signal will be considered a signal in the "time" domain, and each window will be referred to as representing a series or sequence in the "time-domain."

A.4 Object Recognition

The next step involves recognition of "objects" in the 1-D signal. This step involves identifying windows having similar "characteristics" or "features" and grouping those windows with similar characteristics into an "object." The following computational steps are involved in the feature recognition and aggregation into an "object":

(a) Transform the Windowed Data Sets: The window data itself could be used to identify windows with common features (such as through cross-correlations or other processes to look for similarities in time sequences). However, it is believed more efficient to use a fast transform algorithm of the time series data (step 200 and 300, FIG. 1), such as using a discrete Fourier transform (DFT) as coded in a fast Fourier transform (FFT). The reasons for selecting DFT are as follows:
(i) DFT is computationally fast to compute (n log n).
(ii) DFT is an Euclidean distance preserving transformation.
(iii) DFT is an orthonormal transformation.
(iv) DFT is a symmetric transformation (hence, memory efficient).

Other transform techniques can be utilized, such as discrete cosine transform, slant transform, various wavelet transforms, etc. The object of the transform is to identify common or similar properties of the time windows in a different domain. While the transform attributes are present in the time-domain data, the transform simply makes it easier to identify and group or cluster those windows displaying a desired common behavior (such as common stable harmonic behavior).

The transformed Fourier points will be clustered to identify windows having similar frequency or harmonic content. However, it may not be necessary to utilize all the Fourier coefficients. The Fourier transform is a complex transform, having real and imaginary parts. For each window of length "w" a DFT of size "w" can be utilized. FIG. 7 and FIG. 8 demonstrate two windows of interest extracted from the zig-zag one-dimensional signal extracted from the frame depicted in FIG. 1. FIG. 9 and FIG. 10 represent the real part of their corresponding Discrete Fourier Transform of size w=16 each (the window length).

Most of these windows display a skewed energy spectrum, with the majority of the energy contained in the first few Fourier coefficients. The amplitudes of the real part of the transformed signal for the windows presented in FIG. 7 and FIG. 8 are shown in FIGS. 11 and 12. FIG. 13 and FIG. 14 show the coefficients that contain approximately 80% of the energy of these windows. To increase computation efficiency, it may be desirable to preserve only the first few frequency coefficients in the remaining steps of the "object" recognition, that is to depopulate the Fourier coefficients by truncation. For the remaining discussion we will assume the Fourier coefficients have been depopulated and will assume for discussion purposes that the first 4 (k=4) coefficients were used (step 400, FIG. 1).

Each window of size w now is represented by its Fourier coefficients (with or without depopulation). Each coefficient of the transform is a complex number with corresponding real and imaginary parts. If k is the number of Fourier coefficients that have been chosen to represent the window in Fourier domain, a window becomes a point in 2k dimensional "feature" space.

(b) Cluster the Fourier Coefficients in Feature Space: The next step is to cluster the points (the transformed window sequence) in 2k dimensional feature space (step 600 FIG. 1). The points are clustered by requiring that they are "close" in feature space.

Distance between points is measured by a suitable metric (Euclidian metric, L2 metric, etc.) and the cluster neighborhood is established by requiring that the distance ("DIS") between any two clustered feature points is no greater than a chosen constant distance. A cluster represents windows having "close" frequency content. Note that some windows may not fall in a cluster (in which event, there is no "object" associated with that window). Once the clusters are formed, the next step is to identify "objects" within each cluster, that is, those windows that are close spatially in the time-domain. Each cluster may be composed of a number of objects.

(c) Identify Objects: Objects are those windowed series that are contained in the cluster and are spatially adjacent, that is, an object is a portion of the 1-D signal meeting certain criteria. Two windows (a) and (b) are spatially adjacent if: (1) window (a) and window (b) have at least one data point in common (some overlap); or lacking an overlap, (2) the ending point of window (a) is adjacent the starting point of window (b) in the time-domain (step 700, FIG. 1).

Hence, at the completion of this step, sets of windows from the 1-D signal have been organized into "objects," where the windows in a particular object display similar frequency characteristics (or similarity in the selected transform attributes) and are overlapping or adjacent in the time-domain. Each object thus represents a contiguous portion of the 1-D time-domain sequence, that is, each object is contained in series of windows where each window in the series is adjacent to at least one other window in the series, where this series of windows was contained in a single cluster. This set of windows is considered a set of adjacent image windows.

A.5 Form Object Descriptors

The next step is to identify characteristics or descriptors of these objects (step 900-1000, FIG. 1). These descriptors will be used to match or track objects in adjacent frames.

The windowed time sequences associated with each "object" are enclosed in a convex hull enclosing the region (step 902, FIG. 1). It is desired to use the same convex hull shape for every object, such as triangle, square, or rectangle, in order to extract common descriptors later used. Other common enclosing shapes could be used, such as circles or ellipses, which technically are not convex hulls. A preferred convex hull is the Minimum Enclosing Rectangle (MER), which is a rectangle of minimum area that encloses a shape. FIG. 21 shows a portion of the 1-D signal enclosed in a MER. A MER can be uniquely identified by the following geometric descriptors:

(i) Orientation Angle: The angle which the length of the MER makes with the horizontal x-axis in Euclidean space.
(ii) Aspect Ratio: The ratio of breath/length.
(iii) Length of the MER,
(iv) Center position of the MER in x-position and y-position in feature space.

For each object, the technique determines the MER in the time-domain that encloses the time sequence windows that comprise the object and determines the geometric descriptors for the calculated MER (step 903, FIG. 1). These descriptors will be employed for positional and shape error vector in subsequent frames as described in the next section.

While descriptors were formed from the shape of the MER enclosing the object, descriptors from the object itself could be utilized, bypassing the need for enclosing in a common shape. For instance, object features could include object center of gravity, object center, longest straight line through the object, and angle of the longest line.

A.6 Identify Corresponding Objects, Object Tracking

After obtaining the MER descriptors for all objects in all clusters for a particular frame (considered the "reference frame"), the above procedure A2-A5 is repeated for the next adjacent frame ("next adjacent frame" is one from the depopulated frame set). Each frame should be using the same "distance" constant for clustering and use the same frequency depopulation criteria (if used) so that the procedure in the reference frame and the adjacent frame are identical. After completing step A2-A5 for the adjacent frame, each frame will have a series of objects with respective MERs and descriptors. The numbers of MERs in the two frames do not have to match. The procedure now tries to identify an object in the reference frame with a corresponding object (a matching object) in the adjacent frame, that is, to track objects in the two frames. The descriptive MER information is used as matching criteria. The process compares these descriptors (or a subset of interest) for the MERs in the reference frame with MER descriptors in the subsequent adjacent frame [in one embodiment, the comparison is undertaken in the increasing order of the MER occurrence using the center position of the MER (in the time sequence) as the ordering criteria]. (Step 1100-1200 FIG. 2) In one embodiment, the descriptors are compared in the following order:

(1) Aspect Ratio (scale invariant);
(2) Orientation Angle (rotational invariance); and
(3) Length of the MER.

The order can change, and not all descriptors need be used for the comparison.

Objects in two different frames are considered as corresponding or as representing the same feature if the descriptors are within a designated "error" of each other. The error represents the distortions of the subsequent frame with respect to the reference frame. In one embodiment, a percentage of 20% of the reference value was allowed for the error—hence, if all three criteria are such that 0.8×value (reference descriptor)<value (subsequent descriptor)<1.2× value (reference descriptor), the objects were identified as the same feature. Obviously, the error percentage does not have to be the same for each descriptor, and indeed, each error could be weighted and a match declared if the weighted error was within the allowed tolerance. Some objects may not be matched, in which case, no error vector will be computed for that object or its associated MER.

A.7 Formation of Error Vector

Figure 2:
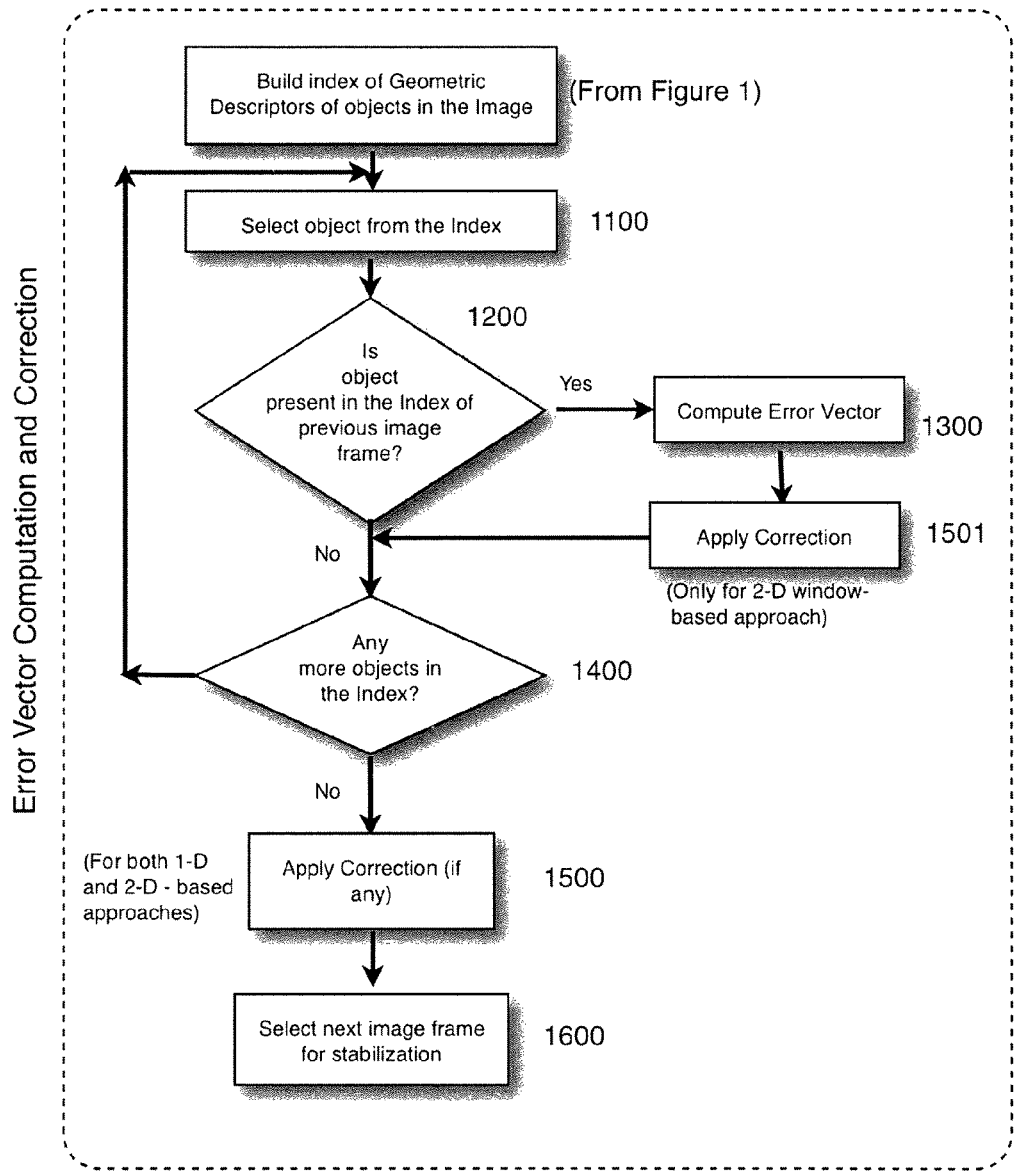
FIG. 2: Is a flow chart showing the method steps involved in tracking objects by comparing the descriptors, and correcting the frames with an error vector
Figure 3:
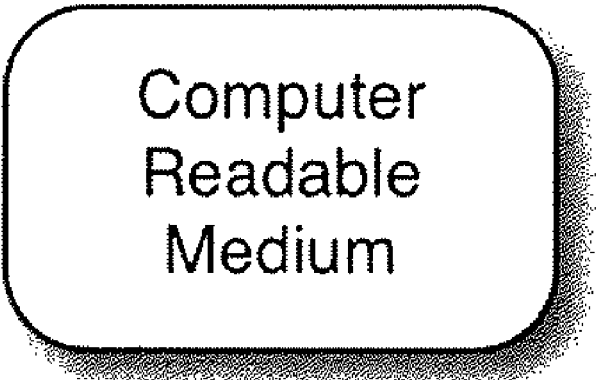
FIG. 3: Is a diagram showing the computer readable medium with stored instructions 2000.
Figure 1:
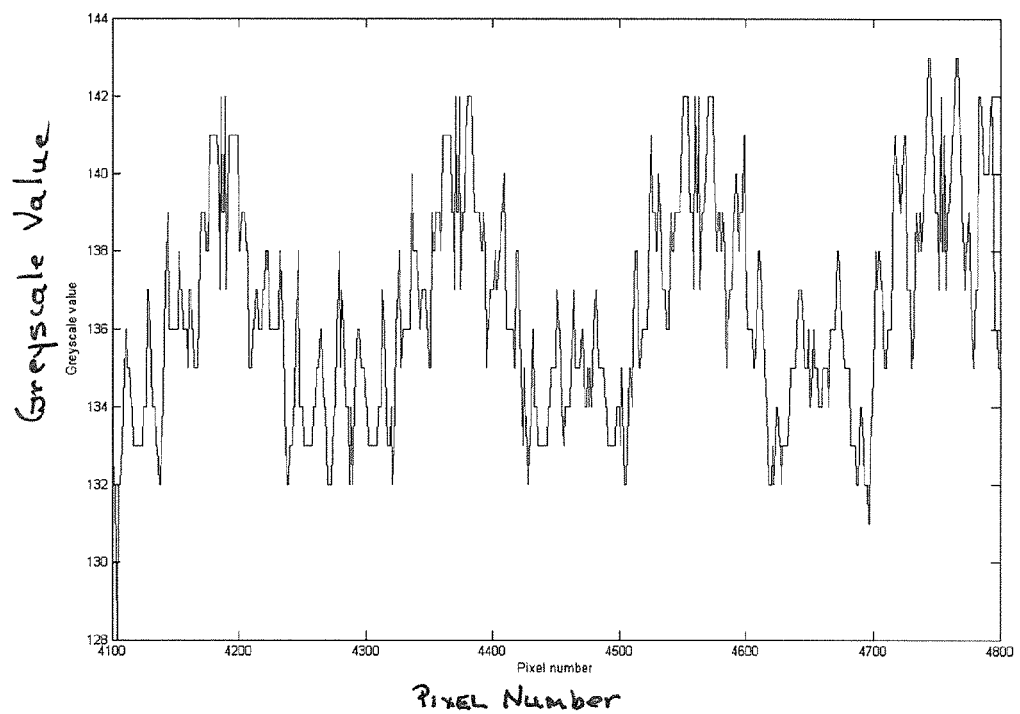

For the objects matched between frames, error vectors are computed locally (step 1300, FIG. 2). The error vectors are calculated in terms of delta-transform, given as follows:

Delta-Orientation Angle=Orientation angle of the matched object in frame 1–Orientation angle of matched object in frame 2.

Delta-Aspect Ratio=Aspect ratio of the matched object in frame 1–Aspect ratio of matched object in frame 2.

Delta-Length=Length of the matched object in frame 1–Length of matched object in frame 2.

Delta-Position=Euclidean distance between the center position of the matched MER in frame 1 and frame 2.

A.8 Stabilization or Correction of the Subsequent Frame

The computed object error vectors are employed to "correct" the image in frame 2 (step 1500, FIG. 2) as follows. The image in frame 2 is divided into generally non-overlapping zones of a particular size, such as 25×25 pixels. The error vector for each zone is calculated by averaging the MER object error vectors for those objects that "appear" in each zone. Because a MER or an object corresponds to a rectangle in the time-domain, a MER (and the associated object) represents a portion of the signal in the frame that appears along a contiguous portion of the zig-zag path. The object itself may represent a smaller portion of the zig-zag path than the MER. Hence, a MER or object can "appear" in more than one zone as the zig-zag path can cross zones. A MER error vector (the object, or portions thereof) must be assigned to a particular zone. Several methods can be used to map or assign a particular object's MER error vector to a zone. For instance, one can assign the MER error vector to (a) that zone that includes the MER center point; (b) the zone with the greatest percentage of the pixels of the MER (or alternatively, the object) if the MER appears in several zones; or (c) assign a weighted MER error vector to each zone containing a part of the MER, for instance, weighted by the percentage of the MER within the particular zone. The two-dimensional zone (a portion of the image frame) is then corrected using the averaged error vector. Corrections can be undertaken for translations, rotations, scaling or other types of MER descriptors. Not all errors need be accounted for and corrected, for instance, rotational errors might be ignored in certain types of data sets.

Obviously, the correction or stabilization technique may require reposting the "stabilized" zone to pixel locations, in which case a suitable interpolation algorithm could be utilized, such as bilinear, spline, etc., to effect the needed re-posting.

The same procedure is applied to the remaining zones of the image frame—each zone is correspondingly corrected by its computed error vector.

Final Frame Tune Up

If the corrected zones have regions that overlap, the overlapped regions are averaged together. For zones of the image without MER error data (for instance, no objects were found in this zone), the zone can be copied to a corrected image or a background can be inserted in the corrected image, such as a "black" background or a background reflecting the average intensity in the frame.

Repeat Procedure for the Next Frame (Step 1600, FIG. 2)

The procedure is then repeated for frame 3, using frame 2 as the new reference frame. In correcting frame 3, it is preferred that the uncorrected or unstabilized frame 2 be used as the reference frame to avoid the propagation of errors in the stabilization process.

FIG. 15 demonstrates the correction of adjacent frames, where only translation errors were accounted for. FIG. 16 shows the percentages of MER matched in zones described in FIG. 15. As can be seen, the percentage of matched MERs in each zone differs.

In real-time processing, it may be desired to correct both frames (the reference frame and the subsequent frame) by ½ the error vector values, that is, to spread the error between the two frames instead of assigning all movement error to the subsequent frame.

B. Parameter Sensitivity in the 1-D Embodiment

Analysis was performed on confocal image video to explore parameter sensitivity. Since the degree of object matching between frames is proportional to the number of discovered unique MERs from an image frame, it is important to measure and evaluate the effect of various parameters of our computational steps on the number of unique MERs obtained for the variations in the selected values of the parameters.

B.1 Effect of Number of Fourier Frequency Components Considered for Clustering on the Number of MERs Generated FIG. 17 demonstrates the effect of increasing the number of Fourier frequency coefficients on the total number of MERs generated. The clustering is done in 2N dimensional space, where N is number of frequency coefficients obtained from FFT. As N is varied (keeping other algorithm parametric constraints constant, such as window size, cluster size and distance between the windows), the number of MER's generated varies with changes in the number of Fourier frequency components selected. The window size for these results was 16 and the clustering Euclidean distance used was 500. As can be seen in FIG. 17, as N is increased, the MER's generated (that corresponds to the number of objects found in feature space) increases. This is due to the fact that when N is increased by a single value the dimensions for clustering increases by 2. Due to addition of more dimensions, some of the feature points forming clusters in 2N dimension space split up and form separate clusters in 2(N+1) dimension space. But at the same time the MER's obtained have better relative stationary harmonic behavior.

B.2 Effect of Number of Fourier Frequency Components Considered for Clustering on the Time of Execution of Similarity Matching FIG. 18 demonstrates the effect of increase in number of frequency components for clustering on the time of execution of the similarity matching process. Clustering accounts for a substantial amount of the run time for the stabilization process, and the time spent in clustering depends on value of N. Since the images under consideration have a skewed energy spectrum, most of the energy is present in the lower frequency initial coefficients of the FFT. Hence, there is little to be gained in increasing the value of N significantly. By increasing N, more discrimination in objects occurs, but at the stabilization process run time increases. For the confocal images examined, N=2 was suitable for clustering as the quality of MER's at N=3 or 4 did not change significantly. The choice of the number of Fourier components, and the depopulation used, if any, will be data dependent.

B.3 Effect of Cluster Size on Number of MERs and Execution Time

FIG. 19 demonstrates the effect of size of cluster on the number of MERs and execution time of the matching process. The number of MERs generated depends on the cluster size. For this analysis, the window size was 16 and N=2. As the clustering size increases the number of MERs obtained reduces. At cluster size of 1000, the numbers of MERs obtained are almost negligible. Cluster size also affects the time used by the algorithm greatly; as the cluster size is increased, the algorithm takes less time to execute. By increasing the cluster size (or the cluster criteria), fewer MERs are obtained and run time or execution time is reduced. If there is a large number of clusters, more computation is needed to generate the MERs and manipulate the MER descriptors. A large number of MERs utilize additional memory, which is not desired. However, if there are too few MERs, the possibility of missing out some important features in the image increases. Obviously, if the technique is used to stabilize images after image acquisition (that is, not in "real-time") the concern with algorithm speed becomes less of an issue.

B.4 Effect of Window Size on the Number of MERs and the Execution Time for Similarity Search FIG. 20 shows the effect of increase in window size to the number of MERs generated and the similarity matching execution time. In this analysis, N=2 and cluster size of 700 (the Euclidian distance in the Fourier domain). In varying the window size, it was found that an increase in window size increased the run time for Fourier transformation, and the number of MER's generated also increased.

II SECOND EMBODIMENT

Using a 2-D Signal

This embodiment is similar to that of the 1-D signal embodiment, and the description will concentrate on the differences between the two embodiments.

A.1 In this embodiment, the steps of Image Capturing (A.1) is identical to the 1-D embodiment. Frame data may be depopulated as needed.

A.2 The signal synthesis step in this embodiment is lacking as this embodiment retains the 2-D image as the working signal.

A.3 Signal Partition

For each frame, partition the frame into overlapping 2 dimensional windows (step 100 FIG. 1), where the windows are aligned along a path through the frame. For instance, one embodiment utilized the following horizontally orientated path for traversing the frame (a type of zig zag):

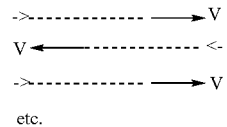

In this embodiment, an 8×8 pixel window was utilized with adjacent windows having an overlap of 5 pixels with the proceeding window, where the overlap is in the direction of movement along the path through the frame, hence, it is not necessary to transform into a one dimensional sequence, thus step 90, FIG. 1 can be eliminated. The window size or length and the degree of overlap are parameters that are adjustable based upon image characteristics.

A.4 Object Recognition (i) Transform each window.

Each window is transformed using a 2-D transform, such as a 2-D Fourier transform (step 200-300, FIG. 1). Other transform techniques can be utilized, such as discrete cosine transform, slant transform, various wavelet transforms, etc. Again, the object of the transform is to identify common or similar desired properties (such as common harmonic behavior) of the time windows in a different domain where the desired property is more readily recognized. Depopulate the Fourier coefficients, if desired (step 400, FIG. 1). In one embodiment, the first three low frequency 2-D Fourier coefficients were utilized (retaining the DC component, and the first "x" frequency coefficient and the first "y" frequency coefficient). Each depopulated Fourier representation of a window is considered a point in k dimensional feature space. With three Fourier components, k is 3×2 (if k is considered a space of complex points) or 3×2×2, if k is considered a space of real points. Each transformed window is associated with the window location, such as by recording window number or window location (such as the window center, window four corners, etc.) (step 500 FIG. 1).

(ii) Cluster the points in feature space (step 600, FIG. 1).

Within this feature space, analysis is undertaken to identify or cluster those points (which represent the transformed windows) which are "close" in the chosen metric or other restraint chosen.

One clustering technique utilized was K-Means clustering. See, e.g., J. Han and M. Kamber, *Data Mining: Concepts and Techniques*, pp. 349-351, Morgan Kaufmann, 2000 (hereby incorporated by reference). K-Means clustering can be undertaken with or without a metric threshold. The preferred K-Means clustering is one without a metric threshold. This allows for the cluster neighborhood size to vary in the feature space. Each formed K-Means cluster is discrete, that is, there is no overlap—a window cannot be in two different K-Means clusters. Other types of clustering algorithms could be used, such as a Euclidian distance constraints similar to the constraint used in the 1-D signal embodiment. When this clustering step is finished, the points in feature space are identified with a cluster. Again, not all points may fall in a cluster.

(iii) Identify the "Objects" in the 2-D (x,y) Domain contained in each Cluster.

An object is a portion of the signal in the (x,y) domain that is contained within windows that transform into the cluster under consideration, and those windows are "close" to each other in the (x,y) domain. An object is thus a portion of the image meeting certain criteria. A window is close to another window if the two either share common pixels (i.e., overlap in the (x,y) domain) or are adjacent in the (x,y) domain: window (a) is adjacent to window (b) if at least one point or pixel of window (a) is adjacent to at least one point or pixel of window (b). (Note, this measure of closeness could also be used in the first embodiment.) Other definitions of "closeness" could be utilized, such as center of gravities of the windows are within a given distance of each other, etc. (step 700, FIG. 1).

An object within a cluster hence represents a portion of the image composed of a series of windows where (1) windows that are "close" in the image frame, and by nature of the clustering; and (2) the signal within the windows display similar harmonic or frequency behavior.

Note that one cluster may have a series of objects, but each object can appear in only one cluster (as the clusters are distinct and discrete).

A.5 Form Object Descriptors (Step 900, FIG. 1)

(i) For each 2-D Object, find the Minimum Enclosing Rectangle (again, other enclosing figures can be utilized (step 902, FIG. 1). Note that the MER can, and usually will, include windows that were not identified with a particular object, and MER's can overlap from object to object.

(ii) For each MER, compute the choses MER characteristics or descriptors (which can include object descriptors) (step 903, FIG. 1) such as:

(a) Geometric center for MER (average (x,y)) of pixels composing the MER);
 (b) Average of the window centers of the MER;
 (c) Size of object in the MER (pixels in object/pixels in MER) or size of MER (pixels in MER/pixels in frame):
 (d) Aspect ratio of MER (Length/Width):
 (e) Length of MER;
 (f) Orientation angle of the MER; and
 (g) Average 2D Frequency composition of Object. For each object, compute the average 2D—frequency composition of the windows that compose the object, including DC. Thus, if three Fourier coefficients were used for each window, the average frequency composition will also have three components, each component being an average for those windows in the object (step 1000, FIG. 1).

A.6 Identify Corresponding Objects, Object Tracking

This step attempts to match or track objects between adjacent frames, that is, to identify an object in the adjacent frame which corresponds to (is similar to) an object in the reference frame. An object in frame n (object(n)) is considered to be corresponding or to track or "match" an object in frame n+1 (object(n+1)) if the object or MER descriptors are "close" (step 1100-1200, FIG. 2). Again, closeness depends on the selected metrics and the allowable "error." For instance, some metrics that could be compared are:

(i) DIS (avg. freq obj (n)–avg freq obj(n+1))<constant1 (say 20%), (close in frequency content, this constraint can be more restrictive that that used in clustering);
 (ii) DIS (geometric center object(n)–geometric center object (n+1)<constant2, (close in center location); and
 (iii) DIS (% frame object (n)–% frame object (n+1)) <constant3, (close in size).

Note not all objects will be matched with a corresponding object, as new objects may be appearing in the adjacent frame, and previous objects may be disappearing in adjacent frames (adjacent in the depopulated frame set) etc.

A.7 Formation of Error Vectors

For the corresponding objects, compute an error vector or difference vector using the chosen tracked characteristics, such as geometric center (x,y) position differences, scale differences (aspect ratios), orientation angle, etc. (step 1300-1400, FIG. 2)

A.8 Stabilize or Correct (Step 1500 or Step 1501, FIG. 2)

Each object comprises a set of pixels in the (x,y) plane. These object sets will be individually corrected.

(a) Discrete Objects (No Overlap)

For each object in frame n+1 which has no overlap with other matched objects in frame n+1, the pixels which comprise the object will be adjusted by applying the difference error vector to these pixels, such as translation (change in geometric center), scale (change in aspect ratio—a shrink or expansion about the geometric center), and other error characteristics thought relevant. Generally, no correction is made for frequency content (other than a possible scaling correction). With rotation or aspect ratio modifications, pixel locations may have to be reposted, as the "new" location may not lie on a pixel position. In this case, a 2-D interpolation scheme can be used to move a point to a pixel location, such as through biquadratic interpolation, bilinear interpolation, spline interpolation, or other interpolation schemes.

(b) Objects with Overlap

If there is an overlap between objects in frame n+1, the errors could be averaged in the overlapped region and the overlapped region corrected by the averaged error. However, an alternative procedure is to partition overlapping objects into new discrete non-overlapping objects, that is, to redefine the objects. The procedure is as follows: for overlapping object a and object b, the overlapped region will be assigned to one object (either a or b) and removed from the remaining object. The overlapped portion is a percentage of object a and a percentage of object b (such as by pixel count, area, etc.). Assign the overlapped region to the object where the overlap forms a larger portion of the object. That is, assign the overlapped region to the object where the region makes a larger contribution to the area or composition of the object.

(c) Objects with No Corresponding Object or Match

Not all objects identified in frame n+1 will have corresponded or be matched with an object in frame n. One procedure would be to simply copy or repost these objects to the new image, with no modifications. Another procedure is to correct this area with an error vector which is the "average" of the surrounding objects. Two procedures were implemented.

Find objects "close" to unmatched objects (say geometric distance from object<constant). For these close objects, identify those objects which have associated error vectors (i.e., the objects that were matched with objects in the prior frame).

Procedure 1—take the errors from the close objects and weights the error by the distance between the close object and the unmatched object, and applies the averaged weighted error to the unmatched objects pixels. For instance, for translation correction, compute [(translation error of nearby object 1)/(distance to object1)], [(translation error of nearby object 2)/(distance to object 2)], . . . and apply a translation of the average of the weighted errors as the translation correction for the unmatched object's pixels.

Procedure 2—Take the errors for the close matched objects and weight these error vectors with the normalized area of the objects associated with the errors. For instance, assume object 1, object 3 and object 10 are close to unmatched objects to be corrected and that object 1 is 576 sq pixels in size, object 3 is 192 sq pixels in size, and object 10 is 448 sq pixels in size. Error vectors associated with object 1 will be weighted by 576/(576+192+448) or 0.47, object 3's errors will be weighted by 0.16, and object 10 by 0.37. The error to be applied to the unmatched objects pixels is the sum of the errors of the weighted error vectors.

Final Frame Tune Up

For areas of the frame that have overlapped corrected objects, the technique can average the overlapped areas, either a weighted or non-weighted average. For areas of the frame that have no objects present, a black background could be posted in the processed image, area could be reposted with no alterations, or the average intensity of image for the frame to this area could be posted (an average "gray").

Repeat procedure for next frame (steps A3-A8) using uncorrected frame n+1, with frame n+2 (step 1600 FIG. 2).

Although the present invention has been described in terms of specific embodiments, it is anticipated that alterations and modifications thereof will no doubt become apparent to those skilled in the art which are intended to be included within the scope of the following claims.

The invention claimed is:

1. A method for correcting a series of digital images for distortions caused by movement of the imaged subject, comprising the steps of:
   (I) selecting a first image:
      (a) partitioning said first image into a series of first image windows, each of said series of first image windows containing a two-dimensional portion of said first image;
      (b) transforming said series of first image windows into a transform domain having transform attributes using a selected transform;
      (c) clustering said transformed first image windows into a series of first image clusters, where each of said transformed first image windows in a particular one of said series of first image clusters reflects similar transform attributes;
      (d) for each of said first image clusters, identifying subsets of said first image windows representing adjacent first image windows that, when transformed, are contained in said first image cluster, each of said subsets of said first image windows considered an first image object; and
      (e) for each of said first image objects, form a series of first image object descriptors;
   (II) selecting a second image:
      (a) partitioning said second image into a series of second image windows, each of said series of second image windows containing a two-dimensional portion of said second image;
      (b) transforming said series of second image windows into a transform domain using said selected transform;
      (c) clustering said transformed second image windows into a series of second image clusters, where each of said transformed second image windows in a particular one of said series of second image clusters reflects similar transform;
      (d) for each of said second image clusters, identifying subsets of said second image windows representing adjacent second image windows that, when transformed, are contained in said second image cluster, each of said subsets of said second image windows considered a second image object; and
      (e) for each of said second image objects, forming a number of second image object descriptors, each having a value;
   (III) for each of said first image objects, identify said second image objects which are corresponding objects, where a particular one of said second image objects is a corresponding object if at least one of said second image object descriptor's values are within a predetermined distance criteria, using a preselected metric, to said corresponding first image object descriptor's value;
   (IV) for each of said corresponding objects, forming an associated error vector representing the distance between a subset of said corresponding object's associated first image object's descriptors and a corresponding subset of said second image object's descriptors; and
   (V) generating a first corrected image from said second image, portions of said first corrected image corresponding to said corresponding objects modified by at least one component of said corresponding objects associated error vector.

2. A computer readable medium having encoded thereon a series of machine executable instructions which when executed by a computer processing system, causes the system to perform the method of claim 1.

3. A method for correcting a series of digital images for distortions caused by movement of the imaged subject, comprising the steps of:
   (I) selecting a first image and converting said first image into a one dimensional first signal:
      (a) partitioning said first signal into a series of first signal windows, each of said series of first signal windows containing a portion of said first image;
      (b) transforming said series of first signal windows into a transform domain having transform attributes using a selected transform;
      (c) clustering said transformed first signal windows into a series of first signal clusters, where each of said transformed first signal windows in a particular one of said series of first signal clusters reflects similar transform attributes;
      (d) for each of said first signal clusters, identifying subsets of said first signal windows representing adjacent first signal windows that, when transformed, are contained in said first signal cluster, each of said identified subsets of said first signal windows considered an a first signal object; and
      (e) for each of said first signal objects, form a series of first signal object descriptors;
   (II) selecting a second image and converting said second image into a one-dimensional second signal:
      (a) partitioning said second signal into a series of second signal windows, each of said series of second signal windows containing a portion of said second signal;
      (b) transforming said series of second signals windows into a transform domain using said selected transform;
      (c) clustering said transformed signal windows into a series of second signal clusters, where each of said transformed second signal windows in a particular one of said series of second signal clusters reflects similar transform attributes;

(d) for each of said second signal clusters, identifying subsets of said second signal windows representing adjacent second signal windows that, when transformed, are contained in said second signal cluster, each of said subsets of said second signal windows considered an second signal object; and (e) for each of said second signal objects, forming a number of second signal object descriptors, each having a value;

(III) for each of said first signal objects, identify said second signal objects which are corresponding objects, where a particular one of said second signal objects is a corresponding object if at least one of said second signal object descriptor's values are within a predetermined distance criteria, using a preselected metric, to said corresponding first signal object descriptor's value;

(IV) for each of said corresponding objects, forming an associated error vector representing the distance between a subset of said corresponding object's associated first signal object's descriptors and a corresponding subset of said second signal object's descriptors; and (V) generating a first corrected image from said second image comprising the steps of:
  (a) partitioning said second image into a series of two-dimensional zones;
  (b) assigning each of said corresponding objects to at least one of said zones;
  (c) for each said zone, form the average zone error vector by averaging said associated error vectors of said corresponding objects assigned to said zone; and
  (d) modify each of said zones based upon at least one component of said zone error vector.

4. A computer readable medium having encoded thereon a series of machine executable instructions, which when executed by a computer processing system, causes the system to perform the method of claim 3.

5. The method of claim 1 wherein step I(b) and II (b) is accomplished using the Fourier transform.

6. The method of claim 1 wherein step I (c) and II (c.) includes clustering by K-means clustering, and said similar attributes comprise frequency content.

7. The method of claim 1 wherein step I (e) and II (e) includes the step of enclosing each said first single object in a first convex hull creating a set of first convex hulls, and enclosing each said second signal object in a second convex hull forming s set of second convex hulls.

8. The method of claim 7 wherein said each said first convex hull forms an enclosing rectangle and each said second convex hull forms an enclosing rectangle and object descriptors comprise an aspect ratio of said enclosing rectangle, an orientation angle of said enclosing rectangle, a length of said enclosing rectangle, a center position of said enclosing rectangle, and combinations thereof.

9. The method of claim 8 wherein said enclosing rectangles are minimum enclosing rectangles.

10. The method of claim 1 wherein said at least one of said second image object descriptor's value is within about 20% of said first image object descriptors values, using a preselected metric.

11. The method of claim 8 wherein said step V includes the step of
  (a) partitioning said second image into a series of two-dimensional zones;
  (b) assigning each of said corresponding objects to at least one of said zones;
  (c) for each said zone, form the average zone error vector by averaging said associated error vectors of said corresponding objects assigned to said zone; and
  (d) modify each of said zones by said zone error vector, and where said average zone error vector comprises at least one of an orientation angle error associated with said average of said enclosing rectangles orientation angles, a length error associated with said average of said enclosing rectangles lengths, a center position error associated with said average of enclosing rectangles center positions, and an aspect ratio error associated with said average of said enclosing rectangle aspect ratios, and combinations thereof.

12. The method of claim 8 wherein said two objects are within said predetermined distance criteria in step III if said predetermined distance criteria is that said second signal object descriptor value is within about 20% of said first signal object descriptor's corresponding value, using said predetermined metric.

13. The method of claim 11 wherein said step of modifying each said zone by said zone error vector comprises transforming each said zone with a transform comprising at least one of said operations of scaling, translation, and rotation using based upon said aspect ration error, center position error, rotation error, or said length error.

14. The method if claim 3 wherein said step of converting said first image and said second image into a one dimensional first signal and one dimensional second signal comprises transforming said first image and said second image using a zig-zag transform.

15. The method if claim 14 wherein said zig-zag transform includes reposting about either columns or rows of an image.

16. The method of claim 3 wherein step I (c) and II (c) includes clustering by K-means clustering, and said similar attributes comprise frequency content.

17. The method of claim 3 wherein step I (e) and II (e) includes the step of enclosing each said first single object in a first convex hull creating a set of first convex hulls, and enclosing each said second signal object in a second convex hull forming s set of second convex hulls.

18. The method of claim 17 wherein said each said first convex hull forms an enclosing rectangle and each said second convex hull forms an enclosing rectangle and object descriptors comprise an aspect ratio of said enclosing rectangle, an orientation angle of said enclosing rectangle, a length of said enclosing rectangle, a center position of said enclosing rectangle, and combinations thereof.

19. The method of claim 18 wherein said enclosing rectangles are minimum enclosing rectangles.

20. The method of claim 18 wherein said average zone error vector comprises at least one of an orientation angle error associated with said average of said enclosing rectangles orientation angles, a length error associated with said average of said enclosing rectangles lengths, a center position error associated with said average of enclosing rectangles center positions, and an aspect ratio error associated with said average of said enclosing rectangle aspect ratios, and combinations thereof.

21. The method of claim 18 wherein said step of modifying each said zone by said zone error vector comprises transforming each said zone with a transform comprising at least one of said operations of scaling, translation, and rotation based upon said aspect ration error, center position error, rotation error, or said length error.

22. The method of claim 1 wherein said digital images reflect intensity or grey level.

23. The method of claim 22 where said digital images represent recordations of confocal microscope images.

24. The method of claim 3 wherein said digital images reflect intensity or grey level.

25. The method of claim 24 where said digital images represent recordations of confocal microscope images.

* * * * *